(12) United States Patent
Ouyang

(10) Patent No.: US 7,254,996 B2
(45) Date of Patent: Aug. 14, 2007

(54) METHOD AND APPARATUS FOR TESTING RUBBER TIRES OR SOLID RUBBER WHEEL LABORATORY SAMPLES

(75) Inventor: George B. Ouyang, Findlay, OH (US)

(73) Assignee: Cooper Tire & Rubber Co., Findlay, OH (US)

( * ) Notice: Subject to any disclaimer, the term of this patent is extended or adjusted under 35 U.S.C. 154(b) by 26 days.

(21) Appl. No.: 11/343,542

(22) Filed: Jan. 31, 2006

(65) Prior Publication Data

US 2006/0169034 A1  Aug. 3, 2006

Related U.S. Application Data

(60) Provisional application No. 60/648,729, filed on Jan. 31, 2005.

(51) Int. Cl.
*G01M 17/02* (2006.01)

(52) U.S. Cl. ............................. 73/146; 451/1; 451/28

(58) Field of Classification Search ................ 73/146; 451/1, 28

See application file for complete search history.

(56) References Cited

U.S. PATENT DOCUMENTS

| | | | |
|---|---|---|---|
| 2,104,436 A * | 1/1938 | Herbert et al. | 451/359 |
| 2,786,526 A * | 3/1957 | Tobey | 451/283 |
| 3,001,334 A * | 9/1961 | Stiegler et al. | 451/1 |
| 3,128,579 A * | 4/1964 | Kehoe et al. | 451/28 |
| 3,134,202 A * | 5/1964 | Hoefler | 451/211 |
| 3,406,489 A * | 10/1968 | Harris, Jr. | 451/488 |
| 4,393,022 A | 7/1983 | Handl | |
| 4,796,328 A | 1/1989 | Horie | |
| 4,918,130 A | 4/1990 | Kano et al. | |
| 4,995,197 A * | 2/1991 | Shieh et al. | 451/28 |
| 6,269,690 B1 * | 8/2001 | Shimizu et al. | 73/146 |
| 6,441,091 B1 | 8/2002 | Leidner et al. | |
| 6,786,800 B1 * | 9/2004 | Delmoro et al. | 451/11 |

* cited by examiner

*Primary Examiner*—Andre J. Allen
(74) *Attorney, Agent, or Firm*—Emch, Schaffer, Schaub & Porcello Co. L.P.A.

(57) ABSTRACT

A method and apparatus for testing rubber tires includes an abrader for rubbing against the surface of the tire and an eraser for removing particles of rubber left on the abrading surface by the tire. The eraser has the capability of absorbing oil or wax included in the tire being tested and in the particles deposited on the abrading surface.

22 Claims, 2 Drawing Sheets

METHOD AND APPARATUS FOR TESTING RUBBER TIRES OR SOLID RUBBER WHEEL LABORATORY SAMPLES

CROSS REFERENCE TO RELATED APPLICATION

The present patent application is based upon and claims the benefit of U.S. provisional application No. 60/648,729 filed Jan. 31, 2005.

The present invention is directed to a method for testing rubber tires including the feature of cleaning rubber compound debris from test surfaces used in such testing and an eraser usable therein.

BACKGROUND OF THE INVENTION

A number of tests are conducted on tires following their manufacture. Among these are indoor tire tests for tread wear including irregular wear, indoor tests for force and moment characterization to confirm the ability of the tire to endure forces expected to be encountered during braking and turning and laboratory abrasion tests for tire tread wear resistance. The tires are subjected to an abrading action longitudinally and laterally with use of an abrading surface. Rotational or other movement of the tire relative to the abrading wheel or other abrading surface results in rubber compound debris accumulating on the abrading surface. The tread rubber compound from which most tires are manufactured have certain amount of oil and/or wax. Particularly for synthetic rubber formulation for tread, such as SBR, large quantities of processing oil is commonly used. It is desirable to immediately remove from the abrading surface such debris and the oil and/or wax contamination accumulated on such abraded surface. The present invention utilizes an eraser wheel for cleaning and removing such debris and oil and wax contamination which is made of a rubber that has no oil and is capable of absorbing the oil and wax typically found in tire tread formulations.

SUMMARY OF THE INVENTION

The present invention utilizes an eraser wheel for cleaning debris from the surface of the abrader which has solution styrene butadiene of rubber (SSBR) for absorbing aromatic processing oil in the rubber of the tread of the tire and ethylene-propylene monomer terpolymer (EPDM) for absorbing wax and paraffinic processing oil. Additionally, it is desirable to utilize a liquid rubber such as Trilene® or LIR 50 or other low molecular weight rubber for the formulation to improve the processability of the oil-less eraser rubber. A non-reinforcing filler, such as soft clay, can be added to the eraser rubber formulation to form a compound having a hardness which is close but on the order of 5 points lower in Shore A hardness than that of the rubber from which the tire was manufactured.

U.S. Pat. No. 4,918,130 discloses an eraser which uses styrene thermoplastic elastomer as the matrix; however, it contains a substantial amount of paraffin or liquid paraffin. U.S. Pat. No. 6,441,049 discloses styrene/ethylene or butylene-styrene block copolymers with approximately 18% by weight of factice such as vulcanized vegetable oil (VVO) which could become a lubricant contaminating the abrading surface.

U.S. Pat. Nos. 4,393,022 and 4,796,328 have as their main ingredients polyvinyl chloride (PVC) and nitrile rubber, neither of which is very compatible with the aromatic processing oils.

The eraser formulation as set forth in the present invention is based on the rubber system similar to that of a normal tire tread compound. The main difference is (i) the processing oil and wax like materials are removed as much as possible, and (ii) the filler and vulcanization are chosen in such a way that the compound hardness and wear rate are in selected ranges. The compound should be softer than the tire tread to ensure complete coverage of the road surface texture for effective cleaning. The degree of reinforcement of the eraser is such that it will wear faster than the tire tread so that more fresh surface can be exposed for absorption and removal of the contaminants, particularly the oil and wax. The wear resistance also is high enough so that frequent replacement of the eraser wheel is avoided to make the test more efficient. Prior art eraser formulations for use in erasing paper are too weak in wear resistance to be a good choice for tire tread abrasion testing and removal of debris from the surface of the abrader.

Following is an example of an eraser formulation suitable for the present invention.

| Eraser Formulation | | |
|---|---|---|
| Rubber | Solution SBR | 80% |
|  | EPDM | 20% |
| To which is added in amounts per hundred parts rubber (PHR) | | |
| Processing aid | Trilene | 15 |
| Activators | Stearic acid | 1.8 |
|  | ZnO | 5 |
| Filler | CaCO3 | 75 |
| Curatives | Sulfur | 2.0 |
|  | MBTS | 2.7 |
|  | Methyl Cumate | 0.1 |
|  | Methyl Ethyl Tuads | 0.5 |

As can be seen, the formulation is made of five parts, which is typical in tire applications. Significant features are listed as follows:

The rubber can include rubbers of the type typically found in tire tread formulation, namely, SBR, BR, NR. SBR is preferred for absorbing and removing aromatic oils. Solution SBR is preferred over the emulsion SBR, because it contains no emulsifier surfactants, which could have lubricating effect. EPDM or EP rubber can be added for better absorbing and removal of paraffinic oils or wax like materials. Additionally, a blend of the above mentioned rubbers may be used for the eraser depending on the tread rubber to be evaluated.

With respect to the other ingredients for the eraser, liquid rubber is to replace the processing oils, typically the aromatic oils. Liquid rubber is a thick oil like material that can make the compound processing much easier. Furthermore, it can be cured into the rubber network, thus making the eraser compound oil-less.

The Trilene is a low molecular weight EPDM made by Uniroyal Chemicals Co. Another suitable material is LIR-50 from Kuraray, Japan. LIR-50 is a low molecular weight polyisoprene with a honey-like consistency.

The filler is added to raise the modulus of the eraser compound close to but slightly softer than that of the tread rubber under evaluation. This is to ensure proper coverage of the road surface texture for effective cleaning. The eraser should wear slightly faster than the tread rubber so that fresh surface can be exposed for more effective removal of the oil and wax contaminants. Therefore, the filler should be the kind that is less reinforcing than the filler found in the tread rubber under evaluation. For example, semi-reinforcing carbon such as N550 or N660 can be used. Non-black filler is preferred for its color. In this case, more reinforcing grades of fine calcium carbonate or clay particles can be used.

The curative system can be either sulfur cure or peroxide cure. The example given above is a mixture of cure systems for SBR and EPDM. The curative system should be adjusted, together with the loading and selection of proper fillers, so that the eraser compound modulus is slightly softer than that of the tread compound under evaluation, for example, 5 point lower in the Shore A hardness. For example, if the tire tread has a Shore A hardness of 65-70, the eraser preferably has a Shore A hardness of 60-65 and as low as 50. The filler and curative system should also be adjusted so that the eraser wear is faster than that of the tread rubber sample wheels, but not too fast. Too fast a wear rate would require frequent replacement of the eraser wheel, which is inconvenient, thus not desirable.

This eraser wheel and method of the present invention will improve over the prior art the effectiveness of (a) indoor tire tests for tread wear, or irregular wear, (b) indoor tire tests for force and moment characterization, and (c) laboratory abrasion tests for tire tread wear resistance.

The problem with prior art tests is mainly due to the poor simulation of the road surface in its roughness and tractive characteristics. A test surface with realistic texture of 0.1 to 0.01 mm is relatively smooth and easily contaminated by degraded rubber, oil and wax from the tread rubber surface. Since the test surface of the abrader is repeatedly used at a fast rate, it will be quickly lubricated by these contaminants, thus affecting the tractive and abrading process, resulting in poor simulation. Degraded rubber (sticky tread skin rubber from fatigue degradation) can be removed by spraying powder, such as talc, wood sawdust, etc.; however, these dust particles are not effective for removing thin layers of oil or wax contaminations.

The eraser wheel of the present invention is designed for effective and efficient removal of these small molecule contaminants from the abrading test surface.

Heretofore the industry did not have an effective method for cleaning oil and wax contaminants from the abrading test surface; therefore, the tire industry has been forced to use very coarse surfaces. Most common practice is to use the very coarse 3M Safety Walk material, with grit size around 80, for simulating the road surface. This is a sand-paper like material having large particles with sharp asperities for providing the grip. The test results become more repeatable, because the road grip provided by sharp asperities is less sensitive to oil or wax contaminants. However, the sharp particles have too much change in the surface contact conditions, making the wear and traction processes for testing the tires unrealistic.

In the case of abrasion tests using course grindstone wheel surfaces, attempt of polishing the grindstone surface for better road surface simulation have met with poor results, mainly due to surface contamination problems.

The eraser wheel system of the present invention can effectively and efficiently clean a wearing surface of an abrader with finer and smooth texture, thus better simulating tire road wear and tractive operations. Examples of smoother wearing surfaces in the laboratory test are: (a) by dressing a corundum grindstone with a diamond cutting tool bit, the sharp tips of the asperities can be removed, better simulating the worn surface of gravels found in a road pavement, (b) covering the test surface with smoother sandpaper like materials made of finer and less sharp particles, (c) engraving the steel test drum surface with fine sub-millimeter texture such as fine grooves such that the sharp edges or tips are blunted to simulate worn road surface textures, and (d) use plasma coating of fine particles, corundum or carborundum, on the steel test drum abrader surface to make a wearing surface of fine texture.

The eraser wheel system of the present invention includes an eraser wheel positioned to contact the abrader surface shortly after contact of the sample tire or rubber wheels with the abrader surface. The eraser wheel system is capable of cleaning the test surface of the abrader by rubbing the test surface in either the lateral or the longitudinal direction, using a slip angle or a braking torque, respectively. The eraser wheel is made of eraser material which preferably has the following features:

(i) Use one or a blend of rubbers commonly found in tire treads, i.e. ESBR, SSBR, BR, NR and polyisoprene. The SSBR is preferred for handling aromatic processing oils. Some EPDM rubber can also be blended to help removing paraffinic oil or wax.

(ii) The rubber system is preferably reinforced by soft filler such as clay, calcium carbonate or semi-reinforcing carbon black or the like. The loading of the filler is such that the eraser should be slightly softer than the tread rubber under evaluation. This is to ensure proper coverage of the road surface texture of the abrader surface for effective cleaning. (For example, 3 to 5 points softer in the Shore A. Hardness). More reinforcing grade tread grade carbon black or silica can also be used, but with more reduced loading to ensure softness and reduced reinforcement for faster wear rate.

(iii) In order to make this eraser compound processable, particularly when mineral fillers are used, liquid rubber should be used to replace normal processing aid, such as the aromatic or paraffinic processing oils. The liquid rubber will become part of the rubber network after curing, thus resulting in an oil-less compound. Examples of liquid rubber which may be used are a) Kuraray's LIR 30 or LIR 50, a polyisoprene rubber of 29,000 and 47,000 molecular weight, respectively, with a molasses like consistency, b) Trilene, a liquid EPDM, c) Royal Elastomers' DPR35, 40 or 75, low molecular weight de-polymerized polyisoprene or natural rubbers, and d) a curable peptizer and processing aid, such as Sartomer's RICON P-30/D, a liquid rubber with 1,2 polybutadiene structure.

(iv) The eraser can be cured by either a sulfur or a peroxide curing system. The sulfur curing system normally used in typical tread formulation is preferred. The combination of filler and cure system should provide the eraser compound with the proper hardness together with a wear rate moderately faster than that of the tread compounds under evaluation, say, 25 to 50% faster. The faster wear rate is to ensure that fresh eraser surface is being continuously exposed for more effect cleaning of oil and wax contaminations from the abrader test surface.

Other eraser materials can also be used. For example, ethylene/styrene, styrene/butadiene, styrene/isoprene containing thermal plastic elastomer can be used to make the eraser wheels by injecting molding. It is important not to have any wax, oil, and factice, such as the VVO (vulcanized vegetable oil) often found in paper eraser formulations.

Following the eraser wheel in contacting the abrader surface, the cleaning system has an air jet, blowing on the wearing surface of the abrader for removing the debris from the eraser wheel, which debris is collected by a vacuum cleaner immediately behind.

DETAILED DESCRIPTION OF THE PREFERRED EMBODIMENT(S)

Figure 1:
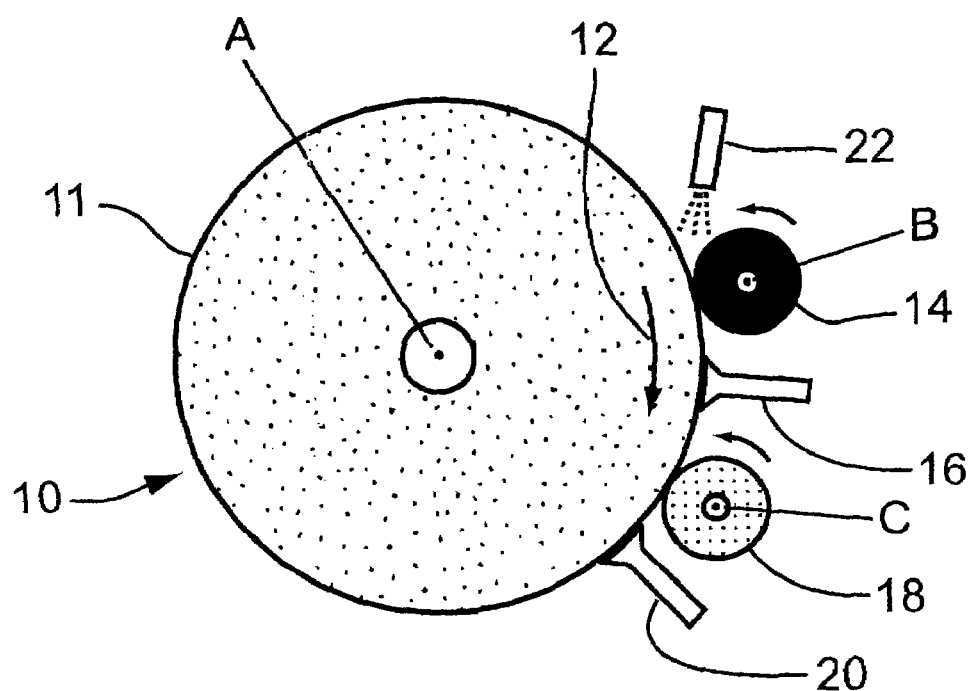
FIG. 1 is a schematic view showing a small rubber sample wheel being driven by a grindstone wheel as part of the testing process.

Referring to FIG. 1, there is shown a grindstone wheel generally designated by the numeral 10 which is shown by arrow 12 to be rotating in a clockwise direction about axis A. A rubber sample wheel 14 is positioned to engage the outer engagement surface 11 of the grindstone wheel 10 and is powered by the grindstone wheel 10 to rotate in a counter clockwise direction as part of the testing process for the sample wheel 14. The outer engagement surface 11 defines a circular path around the circumference of the grindstone wheel. As previously discussed, such engagement by the rotating grindstone wheel 10 against the rubber sample wheel 14 results in rubber debris collecting on the outwardly facing engagement surface 11 of the grindstone wheel 10 engaged by the rubber sample wheel 14. The sample wheel 14 is mounted for rotation about axis B. In order to return such engagement surface 11 of the grindstone wheel 10 to its original condition for further testing of the rubber sample wheel 14 by further rotation of the grindstone wheel 10 against the rubber sample wheel 14, it is desirable to remove such debris from the surface 11 in an attempt to maintain such surface 11 in substantially the same condition for subsequent revolutions while engaged by the rubber sample wheel 14 as it was during initial rotary engagement. Accordingly, there is provided a first vacuum cleaner 16 to vacuum some of the debris from the surface 11. The first vacuum cleaner 16 is positioned adjacent the rubber sample wheel 14 and downstream therefrom.

An eraser wheel 18 is mounted for engagement with the surface 11 of the grinding wheel 10 and is positioned slightly downstream from the first vacuum cleaner 16. The eraser wheel 18 is mounted for rotation about axis C and is formed of the previously discussed eraser material which effectively absorbs oil and wax which may have been in any of the debris left on the surface 11. Immediately downstream from the area of engagement of the surface 11 by the eraser wheel 18 is a second vacuum cleaner 20 to suck up any additional debris and eraser wheel particles which may have collected on the surface 11. Preferably, the eraser wheel 18 is mounted to provide a slight resistance to rotation by the surface 11 so that there is frictional relative movement between the eraser wheel 18 and the surface 11. If desired a dispenser 22 for dispensing a dust powder between the rubber sample wheel 14 and the grindstone wheel 10 may be provided.

Figure 2:
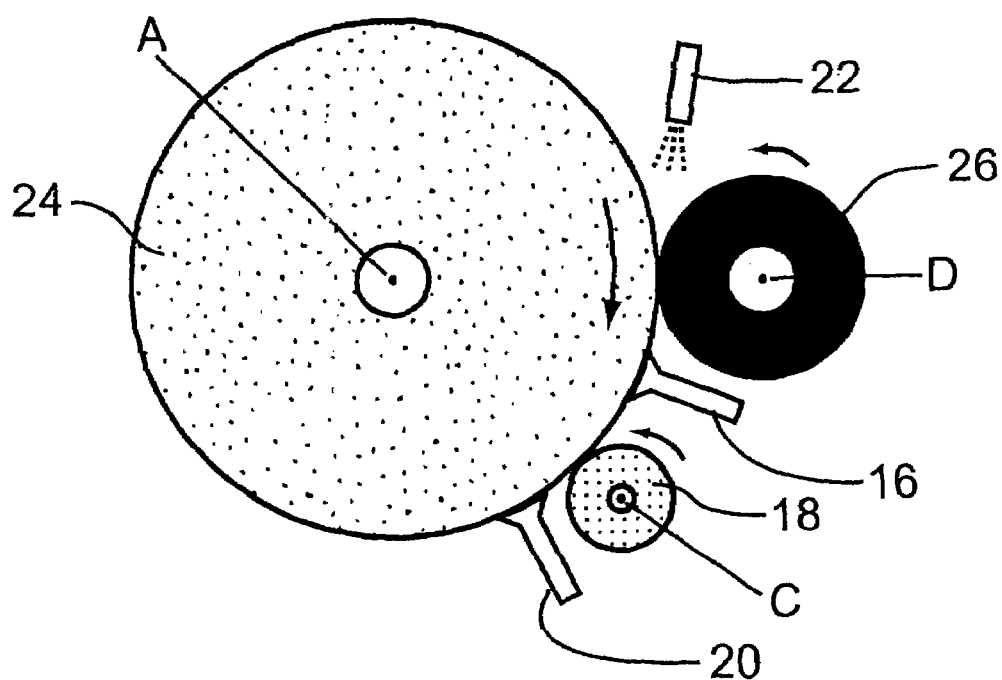
FIG. 2 is a view similar to FIG. 1 showing the testing of a sample tire which is larger than the rubber sample wheel of FIG. 1.

Referring to FIG. 2 there is shown a larger diameter test drum 24 which is similar to the grindstone wheel but is used for testing a sample tire 26. All other elements of FIG. 2 are the same as those described in FIG. 1. The test drum 24 rotates about axis A and the sample tire 26 rotates about axis D.

Figure 3:
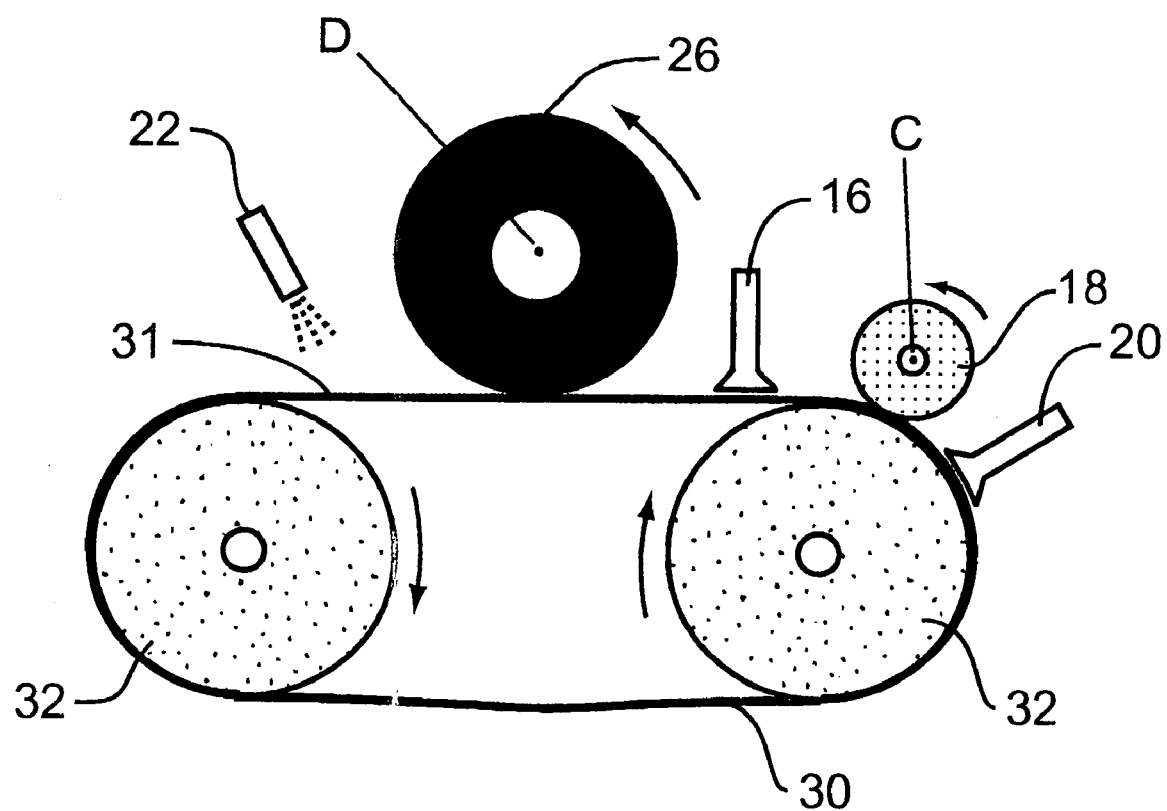
FIG. 3 is a schematic view showing a sample tire being tested on a flat track test belt.

Referring to FIG. 3 there is shown apparatus for testing a sample tire 26 using a test belt 30 which is mounted for rotation by a pair of rotary members 32. The sample tire 26 is engaged to the surface 31 of the test belt 30 and is rotated by such test belt 30 as a result of frictional engagement therewith. As in the previous embodiment there is provided an eraser wheel 18 and a pair of vacuum cleaners 16 and 20, one on each side of the eraser wheel 18. If desired, a dispenser 22 may be provided for dispensing powder between the belt surface 31 and the tire 26.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

The invention claimed is:

1. A method for testing rubber articles including tires, said rubber having oil or wax therein comprising the steps of:
    (a) providing an abrading surface;
    (b) imparting relative movement between said article and said abrading surface, wherein said abrading surface receives thereon particles of rubber having oil or wax;
    (c) providing an eraser having the capability of absorbing oil or wax; and
    (d) imparting relative movement between said eraser and said abrading surface to remove therefrom said particles and said oil or wax.

2. The method according to claim 1 wherein step (d) occurs following step (b) and before step (c).

3. The method according to claim 1 further including the step of vacuuming said abrading surface.

4. The method according to claim 3 wherein the step of vacuuming occurs before step (c).

5. The method according to claim 3 wherein the step of vacuuming occurs after step (d).

6. A method for testing a rubber article having oil or wax in the rubber formulation comprising the steps of:
    (a) providing an abrader;
    (b) imparting relative movement between said article and said abrader, said movement causing particles of rubber to adhere to said abrader;
    (c) separating at least a portion of said abrader from said article;
    (d) providing an eraser formed of a rubber having a formulation with substantially no oil or wax;
    (e) rubbing said eraser against said abrader to remove said particles.

7. The method according to claim 6 further including the step of removing said particles from said abrader and imparting relative movement between said article and the portion of said abrader from which said particles were removed.

8. The method according to claim 7 further including the step of vacuuming to remove said particles.

9. The method according to claim 7 further including the steps of:
    (i) vacuuming said abrader after step (c) and before step (d) to remove at least a portion of said particles and
    (ii) vacuuming said abrader again after step (e).

10. The method according to claim 6 wherein said abrader is a wheel having an abrading surface with a substantially circular cross section and further including the steps of
    (f) rotating said wheel with said article engaged thereto and
    (g) removing said particles.

11. The method according to claim 10 wherein said step of removing includes the step of vacuuming said abrading surface.

12. The method according to claim 10 wherein said step of removing includes a first vacuuming of said abrading surface after step (c) and before step (d) and a second vacuuming of said abrading surface after step (e).

13. The method according to claim 6 wherein said article is a tire and further including the step of mounting said tire for rotation about an axis and imparting rotation to said tire by movement of said abrader while said abrader is in contact with said tire.

14. The method according to claim 6 wherein said abrader is a belt and further including the step of moving said belt against said article.

15. The method according to claim 14 wherein said article is mounted for rotation and further including the step of imparting rotation to said article by engaging said article to said belt and moving said belt.

16. The method according to claim 6 wherein the eraser has a Shore A hardness lower than said rubber article.

17. Apparatus for testing rubber articles including tires comprising:
(a) an abrading surface;
(b) means for imparting relative movement between said article and said abrading surface; and
(c) an eraser positioned to engage and be moved relative to said abrading surface, said eraser having the capability of absorbing oil or wax from said abrading surface.

18. The apparatus according to claim 17 wherein said eraser is positioned to engage said abrading surface immediately following relative movement between said article and said abrading surface.

19. The apparatus according to claim 17 further including one or more vacuum mechanisms for removing particles from said abrading surface.

20. Apparatus for testing a rubber tire comprising:
(a) a rotatable wheel having an abrading surface with a substantially circular cross section;
(b) means for rotating said rotatable wheel while said tire is engaged to said abrading surface;
(c) an eraser engageable with said abrading surface while said abrading surface is being rotated; and
(d) means for removing particles from said abrading surface after said tire is disengaged from said abrading surface and prior to being re-engaged therewith.

21. Apparatus according to claim 20 further including a vacuum head for removing said particles.

22. Apparatus according to claim 20 further including a first vacuum head positioned to remove particles from said abrading surface after engagement between said abrading surface and said tire but before said abrading surface is contacted by said eraser and a second vacuum head positioned to remove particles from said abrading surface after said abrading surface has been contacted by said eraser.

* * * * *